United States Patent
Dubuffet et al.

(10) Patent No.: US 7,534,896 B2
(45) Date of Patent: May 19, 2009

(54) PROCESS FOR THE SYNTHESIS OF PERINDOPRIL AND ITS PHARMACEUTICALLY ACCEPTABLE SALTS

(75) Inventors: Thierry Dubuffet, Autretot (FR); Jean-Pierre Lecouve, Le Havre (FR)

(73) Assignee: Les Laboratories Servier, Courbevoie Cedex (FR)

( * ) Notice: Subject to any disclaimer, the term of this patent is extended or adjusted under 35 U.S.C. 154(b) by 515 days.

(21) Appl. No.: 10/569,537

(22) PCT Filed: Aug. 27, 2004

(86) PCT No.: PCT/FR2004/002197

§ 371 (c)(1),
(2), (4) Date: Feb. 23, 2006

(87) PCT Pub. No.: WO2005/023842

PCT Pub. Date: Mar. 17, 2005

(65) Prior Publication Data

US 2007/0010572 A1    Jan. 11, 2007

(30) Foreign Application Priority Data

Aug. 29, 2003   (EP) ................... 03292132

(51) Int. Cl.
*C07D 209/12*   (2006.01)
(52) U.S. Cl. ............................................... 548/452
(58) Field of Classification Search ............ 548/452
See application file for complete search history.

(56) References Cited

U.S. PATENT DOCUMENTS 7,179,833 B2 *   2/2007   Dubuffet et al. ............ 514/412
7,183,308 B1 *   2/2007   Dubuffet et al. ............ 514/412
7,208,607 B1 *   4/2007   DuBuffet et al. ............ 548/452
7,223,872 B2 *   5/2007   Dubuffet et al. ............ 548/452

FOREIGN PATENT DOCUMENTS

EP   1319668   6/2003
EP   1321471   6/2003

OTHER PUBLICATIONS

M.A. Huffman, et al., "Improved stereoselectivity in the heterogeneous catalytic synthesis of enalapril obtained through multidimensional screening" Tetrahedron Letters, vol. 40 No. 5 p. 831-834, Jan. 29, 1999.
T.J. Blaqcklock, et al., "Synthesis of semisynthetic dipeptides using N-carboxxanhydrides andchiral induction of raney nickel. A method practical for large scale" Journal of Organic Chemistry, vol. 53 No. 4, p. 836-844,1988.
International Search Report for PCT/FR2004/002197, Feb. 3, 2005.
International Preliminary Examination Report and Written Opinion for PCT/FR2004/002197 of Jul. 26, 2006.

* cited by examiner

*Primary Examiner*—Golam M Shameem
(74) *Attorney, Agent, or Firm*—Hueschen and Sage

(57) ABSTRACT

Process for the synthesis of perindopril of formula (I):

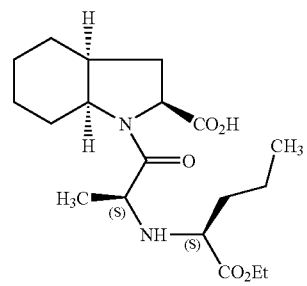

and its pharmaceutically acceptable salts.

7 Claims, No Drawings

PROCESS FOR THE SYNTHESIS OF PERINDOPRIL AND ITS PHARMACEUTICALLY ACCEPTABLE SALTS

The present invention relates to a process for the synthesis of perindopril of formula (I):

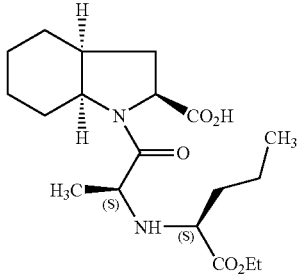

and its pharmaceutically acceptable salts.

Perindopril and its pharmaceutically acceptable salts, and more especially its tertbutylamine salt, have valuable pharmacological properties.

Their principal property is that of inhibiting angiotensin I converting enzyme (or kininase II), which allows, on the one hand, prevention of the conversion of the decapeptide angiotensin I to the octapeptide angiotensin II (a vasoconstrictor) and, on the other hand, prevention of the degradation of bradykinin (a vasodilator) to an inactive peptide.

Those two actions contribute to the beneficial effects of perindopril in cardiovascular diseases, more especially in arterial hypertension and heart failure.

Perindopril, its preparation and its use in therapeutics have been described in the European patent specification EP 0 049 658.

In view of the pharmaceutical value of this compound, it has been important to be able to obtain it by an effective synthesis process, readily transposable to an industrial scale, that leads to perindopril in a good yield and with excellent purity starting from reasonably priced starting materials.

Patent specification EP 0 308 341 describes the industrial synthesis of perindopril by the coupling of (2S,3aS,7aS)-octahydroindole-2-carboxylic acid benzyl ester with N-[(S)-1-carboxybutyl]-(S)-alanine ethyl ester, followed by deprotection of the carboxylic group of the heterocycle by catalytic hydrogenation.

The Applicant has now developed a new process for the synthesis of perindopril.

More specifically, the present invention relates to a process for the synthesis of perindopril and its pharmaceutically acceptable salts which is characterised in that the compound of formula (II):

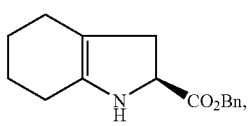

wherein Bn represents a benzyl group, is reacted with a compound of formula (III) having the S configuration:

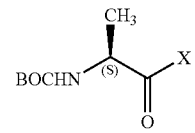

wherein X represents a halogen atom and BOC represents a tert-butoxycarbonyl group, in the presence of a base, to yield, after deprotection of the amino function, the compound of formula (IV):

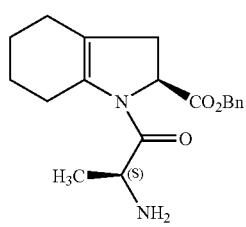

wherein Bn represents a benzyl group, which is reacted with ethyl 2-oxopentanoate under hydrogen pressure, in the presence of palladium-on-carbon, to yield the compound of formula (I) directly.

Among the bases that can be used in the reaction between the compounds of formulae (II) and (III) there may be mentioned, without implying any limitation, organic amines such as triethylamine, pyridine, N-methylmorpholine or diisopropylethylamine, and mineral bases such as NaOH, KOH, $Na_2CO_3$, $K_2CO_3$, $NaHCO_3$ or $KHCO_3$.

The reaction between the compound of formula (IV) and ethyl 2-oxopentanoate is preferably carried out in an alcoholic solvent, under a hydrogen pressure of from 1 to 5 bars, at a temperature of form 20 to 60° C.

EXAMPLE (2S,3aS,7aS)-1-{(2S)-2-[(1S)-1-(ethoxycarbonyl)butylamino]-propionyl}-octahydro-1H-indole-2-carboxylic acid tert-butylamine salt Step A: Benzyl (2S)-1-{(2S)-2-[(tert-butoxycarbonyl)amino]propionyl}-2,3,4,5,6,7-hexahydro-1H-indole-2-carboxylate Introduce 200 g of benzyl (2S)-2,3,4,5,6,7-hexahydro-1H-indole-2-carboxylate and 1.5 litres of dichloromethane into a reactor, then bring the temperature of the reaction mixture to 0° C. and add 107 ml of triethylamine and then 162 g of (2S)-2-[(tert-butoxycarbonyl)amino]propionyl chloride. Subsequently, bring the mixture to ambient temperature. After stirring for 1 hour at that temperature, wash the mixture with water and then with a dilute acetic acid solution. The benzyl (2S)-1-{(2S)-2-[(tert-butoxycarbonyl)amino]propionyl}-2,3,4,5,6,7-hexahydro-1H-indole-2-carboxylate solution so obtained is used as it is in the following Step.

Step B: Benzyl (2S)-1-{(2S)-2-aminopropionyl}-2,3,4,5,6,7-hexahydro-1H-indole-2-carboxylate Introduce the solution obtained in the above Step into a reactor, and then add 133 g of trifluoroacetic acid. After stirring for 1 hour 30 minutes at ambient temperature, wash the mixture with water and then with a saturated solution of sodium hydrogen carbonate and evaporate off the solvents to yield benzyl (2S)-1-{(2S)-2-aminopropionyl}-2,3,4,5,6,7-hexahydro-1H-indole-2-carboxylate.

Step C: (2S, 3aS, 7aS)-1{(2S)-2-[(1S)-1-(ethoxycarbonyl)butylamino]propionyl}-octahydro-1H-indole-2-carboxylic acid Introduce into a hydrogenation vessel 200 g of the compound obtained in the above Step and 88 g of ethyl 2-oxopentanoate in solution in ethanol, followed by 5 g of 10% Pd/C. Hydrogenate under atmospheric pressure at 30° C. until the theoretical amount of hydrogen has been absorbed.

Remove the catalyst by filtration and then evaporate off the solvent. (2S,3aS,7aS)-1-{(2S)-2-[(1S)-1-(ethoxycarbonyl)butylamino]propionyl}-octahydro-1H-indole-2-carboxylic acid is thereby obtained in a yield of 85%.

Step D: (2S, 3aS, 7aS)-1-{(2S)-2-[(1S)-1-(ethoxycarbonyl)butylamino]propionyl}-octahydro-1H-indole-2-carboxylic acid tert-butylamine salt The compound obtained in the above Step (200 g) is dissolved in 2.8 litres of acetonitrile, and then 40 g of tert-butylamine and 0.4 litres of ethyl acetate are added.

The suspension obtained is then refluxed until dissolution is complete, and the solution obtained is subsequently filtered hot and cooled, with stirring, to a temperature of from 15 to 20° C. The resulting precipitate is then filtered off, made into a paste again with acetonitrile, dried and then recrystallised from ethyl acetate to give the expected product in a yield of 95% and with an enantiomeric purity of 99%.

The invention claimed is:
1. A process for the synthesis of compounds of formula (I):

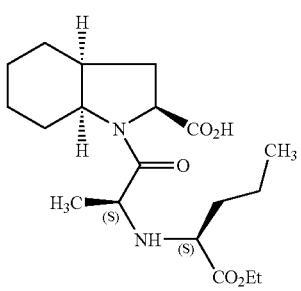

(I)

and pharmaceutically acceptable salts thereof, wherein a compound of formula (II):

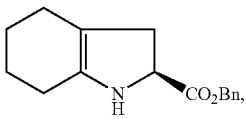

(II)

wherein Bn represents a benzyl group, is reacted
with a compound of formula (III) having the S configuration:

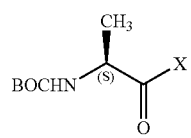

(III)

wherein X represents a halogen atom and BOC represents a tert-butoxycarbonyl group, in the presence of a base,
to yield, after deprotection of the amino function, a compound of formula (IV):

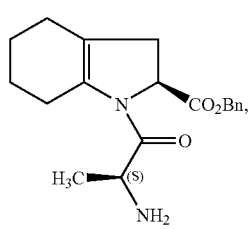

(IV)

wherein Bn represents a benzyl group,
which is reacted with ethyl 2-oxopentanoate under hydrogen pressure, in the presence of palladium-on-carbon, to yield the compound of formula (I).

2. The process of claim 1, wherein the base used for the reaction between the compounds of formula (II) and (III) is an organic amine selected from triethylamine, pyridine, N-methylmorpholine and diisopropylethylamine, or a mineral base.

3. The process of claim 2, wherein the mineral base is selected from NaOH, KOH, $Na_2CO_3$, $K_2CO_3$, $NaHCO_3$ and $KHCO_3$.

4. The process of claim 1, wherein the hydrogenation reaction is carried out in an alcoholic solvent.

5. The process of claim 1, wherein the hydrogenation reaction is carried out under a pressure of from 1 to 5 bars.

6. The process of claim 1, wherein the hydrogenation reaction is carried out at a temperature of from 20 to 60° C.

7. The process of claim 1 for the synthesis of perindopril in the form of its tertbutylamine salt.

* * * * *

UNITED STATES PATENT AND TRADEMARK OFFICE
CERTIFICATE OF CORRECTION

PATENT NO. : 7,534,896 B2  Page 1 of 1
APPLICATION NO. : 10/569537
DATED : May 19, 2009
INVENTOR(S) : Dubuffet et al.

It is certified that error appears in the above-identified patent and that said Letters Patent is hereby corrected as shown below:

Title Page, item [73] Assignee: "Les Laboratories Servier" should be --Les Laboratoires Servier--.

Signed and Sealed this

Twenty-second Day of September, 2009

David J. Kappos
*Director of the United States Patent and Trademark Office*